(12) United States Patent
Bala

(10) Patent No.: US 10,953,123 B2
(45) Date of Patent: Mar. 23, 2021

(54) STERILIZATION PROCESS CHALLENGE PACK

(71) Applicant: American Sterilizer Company, Mentor, OH (US)

(72) Inventor: Harry Bala, South Barrington, IL (US)

(73) Assignee: American Sterilizer Company, Mentor, OH (US)

( * ) Notice: Subject to any disclaimer, the term of this patent is extended or adjusted under 35 U.S.C. 154(b) by 269 days.

(21) Appl. No.: 15/949,756

(22) Filed: Apr. 10, 2018

(65) Prior Publication Data

US 2019/0307911 A1    Oct. 10, 2019

(51) Int. Cl.
| | |
|---|---|
| *A61L 2/28* | (2006.01) |
| *A61L 2/07* | (2006.01) |
| *A61L 2/20* | (2006.01) |
| *C12Q 1/22* | (2006.01) |

(52) U.S. Cl.
CPC .................... *A61L 2/28* (2013.01); *A61L 2/07* (2013.01); *A61L 2/206* (2013.01); *A61L 2/208* (2013.01); *C12Q 1/22* (2013.01); *A61L 2202/14* (2013.01); *A61L 2202/24* (2013.01); *A61L 2202/26* (2013.01)

(58) Field of Classification Search
CPC ... A61L 2/28; A61L 2/07; A61L 2/206; A61L 2/208; A61L 2202/14; A61L 2202/24; A61L 2202/26; C12Q 1/22
USPC ............................................................ 436/1
See application file for complete search history.

(56) References Cited

U.S. PATENT DOCUMENTS

| | | | |
|---|---|---|---|
| 3,752,743 A | 8/1973 | Henshilwood | |
| 5,478,749 A | 12/1995 | Dyke | |
| 5,552,320 A | 9/1996 | Smith | |
| 5,750,184 A * | 5/1998 | Imburgia | C12Q 1/22 427/2.13 |
| 6,551,555 B2 | 4/2003 | Antonoplos et al. | |
| 6,874,634 B2 * | 4/2005 | Riley | A61L 2/26 206/370 |
| 7,045,343 B2 | 5/2006 | Witcher et al. | |

(Continued)

FOREIGN PATENT DOCUMENTS

| | | |
|---|---|---|
| EP | 0202724 A1 | 11/1986 |
| EP | 0421760 A1 | 4/1991 |

(Continued)

OTHER PUBLICATIONS

International Search Report and Written Opinion issued by ISA/EPO in connection with PCT/US2019/026262 dated Nov. 11, 2019.

*Primary Examiner* — Matthew D Krcha
*Assistant Examiner* — Jacqueline Brazin
(74) *Attorney, Agent, or Firm* — Levenfeld Pearlstein, LLC

(57) ABSTRACT

A sterilization process challenge pack including a base tray, a first cover, and a second cover is configured to provide a restrictive flow path for gaseous sterilization medium to test the efficacy of a sterilization process. The base tray includes at least one chamber containing a biological indicator and/or chemical indicator. The first cover including a notch is configured to cover the at least one chamber. The second cover is attached to peripheral surfaces of the base tray except at an unsealed portion. A flow path through the unsealed portion and the notch in the first cover provides the only fluid communication between an external environment and the at least one chamber.

12 Claims, 5 Drawing Sheets

(56) References Cited

U.S. PATENT DOCUMENTS

| | | | | |
|---|---|---|---|---|
| 7,744,832 B2 * | 6/2010 | Horacek | ................ | A61B 50/30 |
| | | | | 422/300 |
| 7,927,866 B2 | 4/2011 | Justi et al. | | |
| 9,017,994 B2 | 4/2015 | Franciskovich et al. | | |
| 2005/0236346 A1 * | 10/2005 | Whitney | ................... | B01L 9/06 |
| | | | | 211/74 |
| 2013/0089922 A1 * | 4/2013 | Franciskovich | ......... | C12Q 1/22 |
| | | | | 435/287.4 |

FOREIGN PATENT DOCUMENTS

| | | |
|---|---|---|
| WO | 9524622 A1 | 9/1995 |
| WO | 2013055569 A1 | 4/2013 |

\* cited by examiner

STERILIZATION PROCESS CHALLENGE PACK

BACKGROUND

The present invention is directed to a sterilization process challenge pack for verifying the efficacy of a sterilization process.

The sterilization of medical equipment, towels (for hospital and operating room use), gowns and the like is carried out, for the most part, using steam sterilization equipment and methods. For example, a bundle of towels is placed into a steam sterilizer, a vacuum is drawn in the sterilizer to evacuate the air, and steam is introduced to sterilize the bundle of towels.

Due to the nature of the towels being "bundled" it may be difficult to assure that the innermost regions (volume) of the towels have been sufficiently subjected to the steam (time and temperature) to assure proper levels of sterilization. Essentially, it is a "challenge" for the steam to be introduced to the innermost parts to effect sterilization.

To this end, "challenge packs" or "challenge kits" have been developed to simulate the bundle and more specifically to simulate the difficulty or resistance in reaching the innermost parts: (1) to effect a vacuum; and (2) to introduce steam sufficient to sterilize the local area. There is in fact an ANSI standard for challenge packs that is based upon a bundle of towels having a specific size.

Presently, there are challenge packs on the market. These include paper stacks (stacked like a deck of cards) with an indicator sheet generally in the middle of the stack that can indicate either that a vacuum has been achieved or that a sufficient amount of steam has reached the indicator pack. Another includes a paper stack with a cut out center with a biological indicator vile in the middle. Still another type of indicator includes a plastic tube that has a hole in one end, is packed with a permeable material (such as a towel or absorbent paper sheet) and an indicator at the opposite end.

U.S. Pat. No. 9,017,994, which is assigned to the Applicant of the present application and incorporated herein by reference, discloses a sterilization test pack including a biological indicator and a chemical indicator. The sterilization test pack also includes at least one external channel providing a restricted flow path(s) to the biological and chemical indicators, in which the at least one channel is defined by a groove(s) or indentation(s) having a depth, a width, and a length.

Accurate verification of sterilization processes is important for obvious reasons. The present disclosure provides an improved sterilization process test pack, which is also referred to as a sterilization process challenge pack herein, that closely mimics the challenge to reach the innermost regions of a bundle of towels used in the ANSI/AAMI ST79 for sterilization challenge packs.

BRIEF SUMMARY

A sterilization challenge pack configured to provide a restrictive flow path into an interior space for a gaseous sterilization medium to verify the efficacy of a sterilization process is provided according to various embodiments.

In one aspect, a sterilization challenge pack may comprise a base tray, a first cover, and a second cover. The base tray may include at least one chamber and a peripheral surface. The first cover may be configured to cover the at least one chamber and include a notch. The second cover may be arranged over the first cover and attached to the peripheral surface of the base tray except at an unsealed portion. The sterilization challenge pack may include at least one sterilization indicator in the at least one chamber, wherein the only fluid communication between the at least one chamber and an external environment is provided through the unsealed portion and the notch.

In an embodiment, the at least one chamber may include a first chamber and a second chamber, which are in fluid communication with each other. In such an embodiment, the at least one sterilization indicator may include a biological indicator and a chemical indicator, wherein the biological indicator may be contained in the first chamber and the chemical indicator may be contained in the second chamber. The first cover may include a first portion configured to cover the first chamber and the second portion configured to cover the second chamber, which are connected by a relatively narrow middle portion.

The base tray may include ledges defined by relatively narrow surfaces recessed from the peripheral surface and arranged between the peripheral surface and the first and second chambers. The first cover may be configured such that when the first cover is place on the ledges, it sits even leveled with the peripheral surface and the notch extends beyond the ledges into the first chamber. In an embodiment, the notch may be provided in the first portion of the first cover proximate an outer peripheral edge, such that the notch may be aligned with the unsealed portion defined between the second cover and the base tray to provide a flow path into the first chamber through the unsealed portion and notch.

The base tray may include a recessed portion between the first and second chambers. In such an embodiment, the first cover may be configured such that when the first cover is placed on the ledges, the middle portion is arranged over the recessed portion. The ledges may have a first depth and the recessed portion may have a second depth that is greater than the first depth to provide a gap between the middle portion of the first cover and the recessed portion of the base tray, which may provide a fluid path between the first and second chambers.

In an embodiment, the unsealed portion may extend from an outer periphery of the second cover to the notch to provide a flow path having a width of about ¼ inch to about 1 inch. The notch in the first cover may be defined by a generally semicircular cut out having a diameter of about ¼ inch to about 1 inch.

In some embodiments, the base tray may be thermoformed from a thermoplastic polymer. The second cover may be sealed to the peripheral surface via an adhesive or heat seal, wherein the second cover is left unsealed to the peripheral surface in the unsealed portion. In an embodiment, the second cover may be formed from a metalized film and heat sealed to the peripheral surface, wherein the second cover is left unsealed to the peripheral surface in the unsealed portion.

In an embodiment, the first and second chambers may be arranged in a substantially parallel side by side relationship, in which a flow path from the external environment to the first chamber is provided through the unsealed portion and notch. In another embodiment, the base tray and/or the first and second covers may be formed from a sufficiently transparent material, such that the at least one sterilization indicator is visible from outside the sterilization challenge pack.

In another aspect, a sterilization challenge pack may comprise a base tray including at least one chamber, a cover, and at least one sterilization indicator contained in the at least one chamber. The base tray also may include a peripheral surface that is substantially flat and free of any channels, grooves or indentations that can provide a flow path between an external environment to the at least one chamber. The cover may be sealingly attached to the peripheral surface of the base tray except at an unsealed portion, wherein the only fluid communication between the at least one chamber and an external environment is provided through the unsealed portion between the substantially flat peripheral surface and the cover.

In an embodiment, the at least one chamber may include a first chamber and a second chamber, which are in fluid communication with each other. The at least one sterilization indicator may include a biological indicator and a chemical indicator, wherein the biological indicator is contained in the first chamber and the chemical indicator is contained in the second chamber. The unsealed portion may extend from an outer periphery of the cover to the at least one chamber to provide a flow path having a width of about 1/32 inch to about 1 inch.

The cover may be sealed to the peripheral surface via an adhesive or heat seal, wherein the cover is left unsealed to the peripheral surface in the unsealed portion. In an embodiment, the cover may be formed from a laminate material having a metal foil layer and a sealing layer, wherein the cover is heat sealed to the peripheral surface except in the unsealed portion.

Other aspects, objectives and advantages will become more apparent from the following detailed description.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

Figure 1:
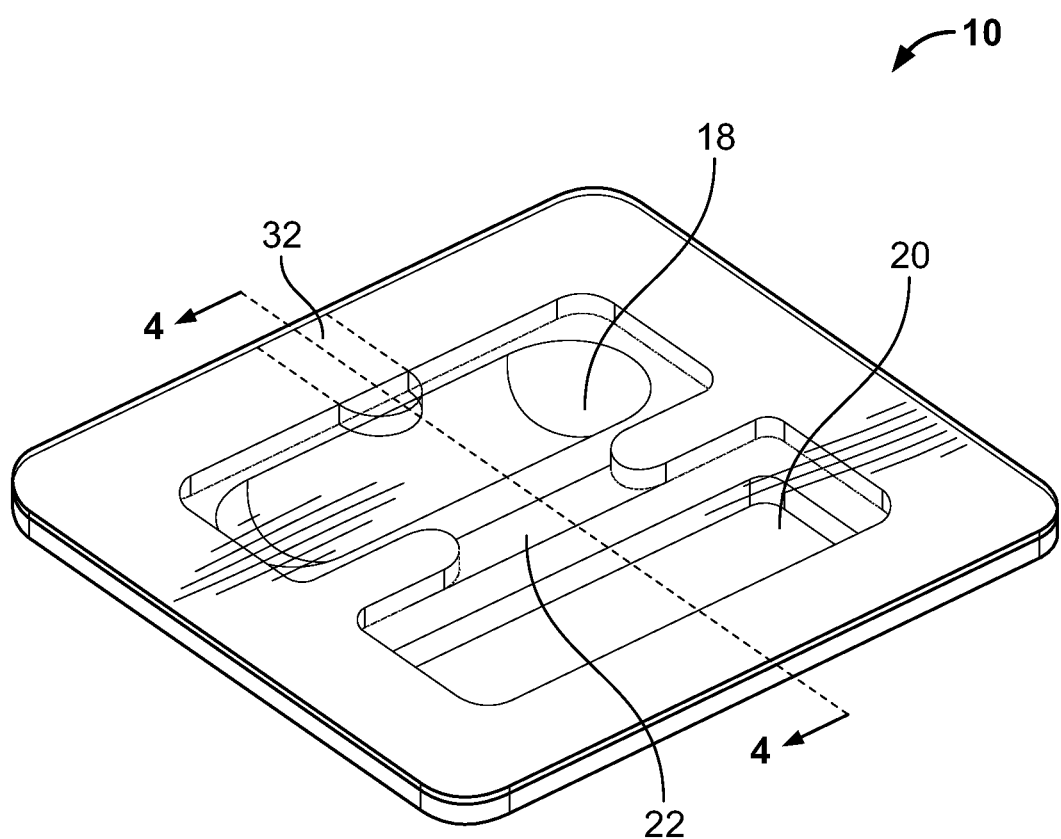
FIG. 1 is a top perspective view of a sterilization process challenge pack according to an embodiment.
Figure 2:
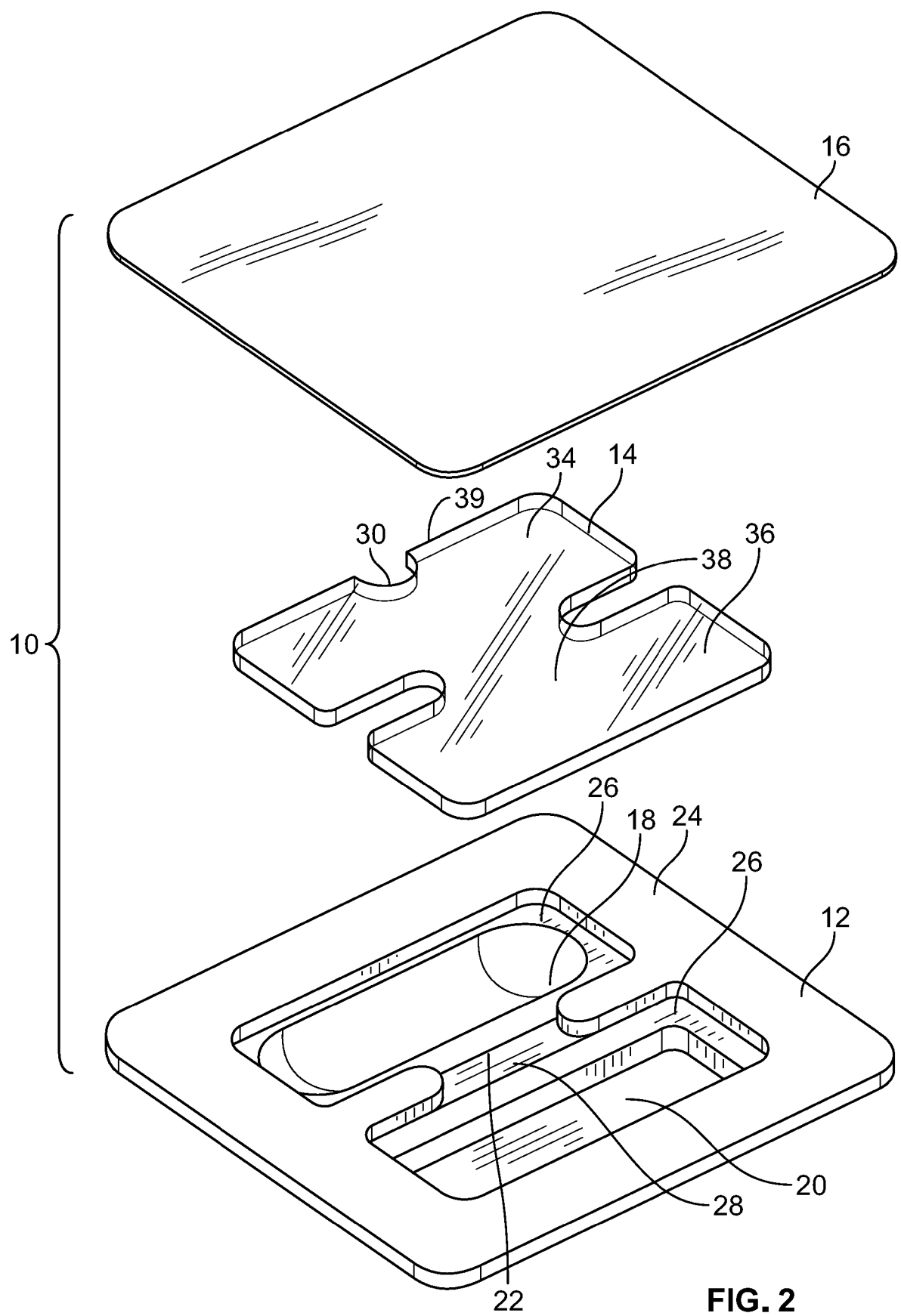
FIG. 2 is an exploded view of the challenge pack of FIG. 1.

For simplicity and clarity of illustration, elements shown in the figures may not be drawn to scale. For example, the dimensions of some of the elements may be exaggerated relative to each other for clarity.

DETAILED DESCRIPTION

While the present disclosure is susceptible of embodiment in various forms, there will hereinafter be described presently preferred embodiments with the understanding that the present disclosure is to be considered an exemplification and is not intended to limit the disclosure to the specific embodiments illustrated.

It should be further understood that the title of this section of this specification, namely, "Detailed Description Of The Invention", relates to a requirement of the United States Patent Office, and does not imply, nor should be inferred to limit the subject matter disclosed herein.

A sterilization process challenge pack according to various embodiments is provided. The challenge pack is configured to test the efficacy of a sterilization process and may include a biological indicator and/or a chemical indicator. For example, the challenge pack may be used to verify a sterilization process involving steam or gaseous sterilization medium/sterilants, such as gaseous hydrogen peroxide, gaseous ethylene oxide, and the like.

The challenge pack may include a biological indicator for verifying the efficacy of a sterilization process, which may contain microorganisms, such as *Escherichia coli*, *Legionella* sp., *Campylobacter* sp., *Staphylococcus*, *Streptococcus* species and *Cryptosporidium*. The challenge pack may also include a chemical indicator configured to verify a sterilization process by indicating whether it has been in contact with the sterilization medium for a predetermined time at a predetermined temperature.

FIGS. 1-4 illustrate a sterilization process challenge pack 10 according to an embodiment. The challenge pack 10 may generally comprise a base tray 12, first cover 14, and a second cover 16. The base tray 12 may include a first chamber 18, a second chamber 20, and a flow path 22 therebetween. The first cover 14 may be configured to cover the first and second chamber 18, 20 and may include a notch 30. The second cover 16 may be sealingly attached to the base tray 12 except at an unsealed portion 32. The unsealed portion 32 may extend from an outer periphery of the second cover 16 to the notch 30, such that a fluid flow path from the external environment into the first chamber 18 may be provided through unsealed portion 32 and the notch 30. In another embodiment, the challenge pack may include only one cover, which may be sealingly attached to the base tray except at the unsealed portion to provide a fluid flow path from the external environment into the first and second chambers.

Figure 5:
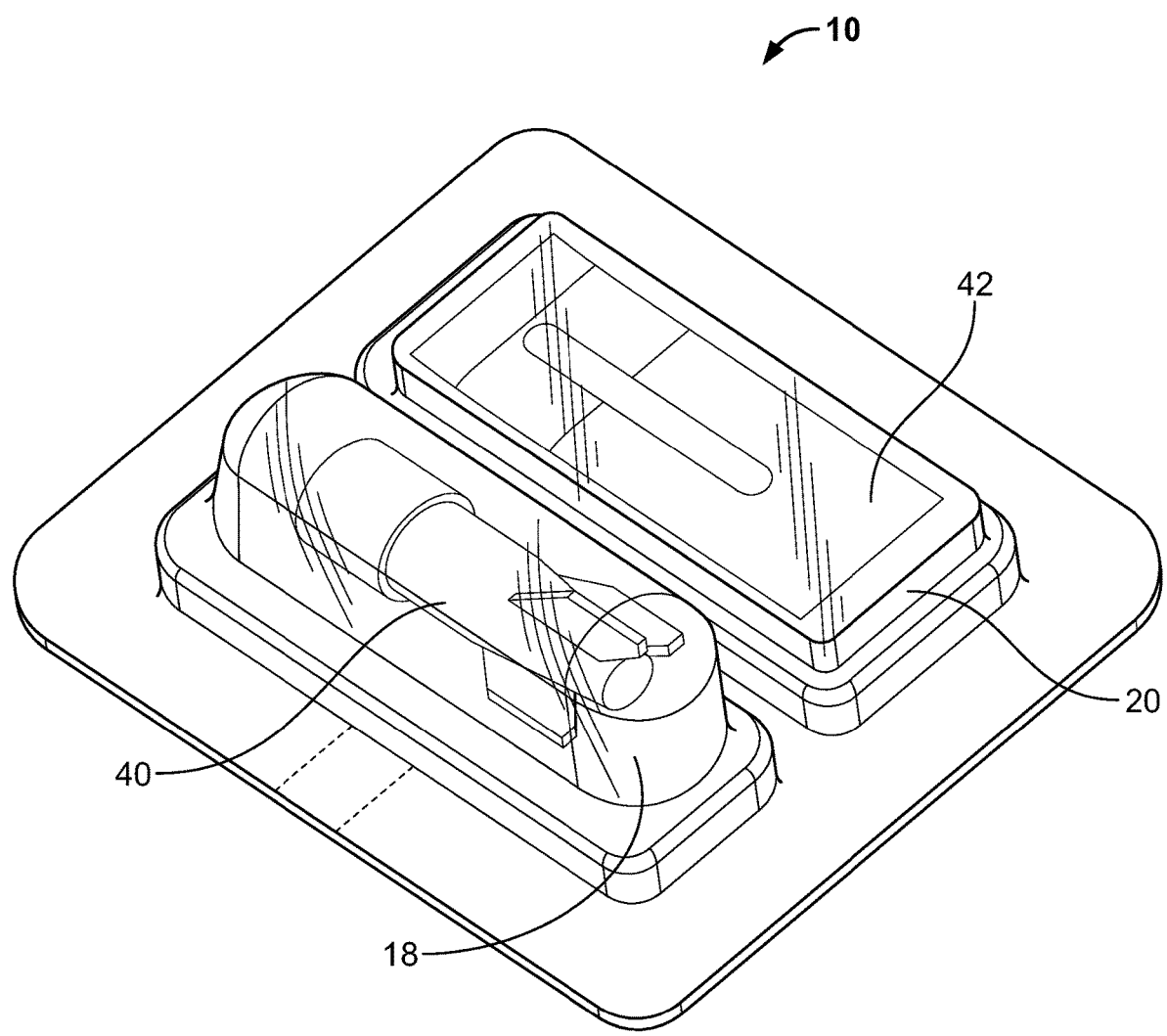
FIG. 5 is a bottom perspective view of the challenge pack of FIG. 1 including a biological indicator and a chemical indicator.

The first and second chambers 18, 20 may be arranged in a substantially parallel side by side relationship. The first chamber 18 may be configured as a deeper/larger chamber for holding a biological indicator, while the second chamber 20 may be configured as a shallower/smaller chamber for holding a relatively flat chemical indicator. For example, the challenge pack 10 may contain a biological indicator 40, such as a self-contained biological indicator (SCBI) in the first chamber 18 and a chemical indicator 42 in the second chamber 20 as shown in FIG. 5. In an embodiment, the first chamber 18 may be configured as a shallower/smaller chamber and contain a chemical indicator and the second chamber 20 may be configured as a deeper/larger chamber and contain a biological indicator. In yet another embodiment, the base tray 12 may include only one chamber configured to contain one or both of biological indicator and chemical indicator.

Figure 4:
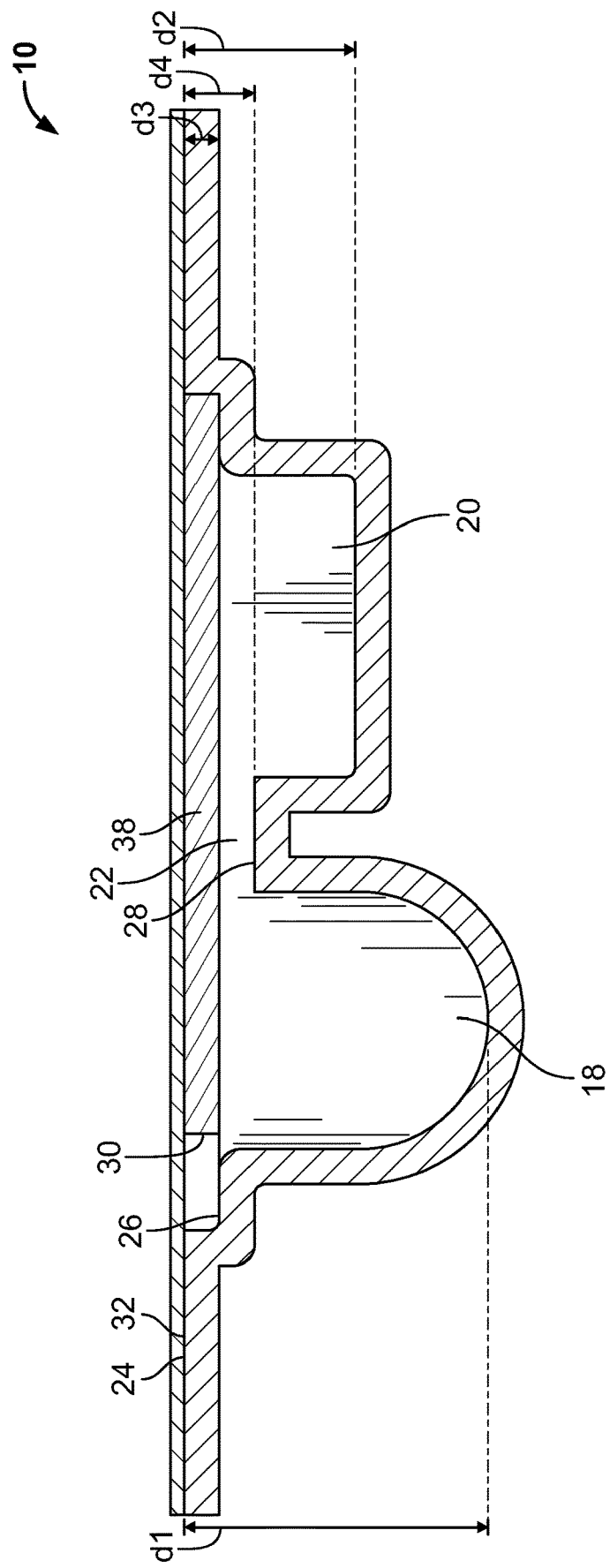
FIG. 4 is a cross sectional view of the challenge pack of FIG. 1 without a top cover layer.

In an embodiment, the base tray 12 may comprise peripheral surfaces 24, the first chamber 18 having a depth (d1), the second chamber 20 having a depth (d2), ledges 26 having a depth (d3), and a recessed portion 28 having a depth (d4). As best shown in FIG. 4, the first and second chambers 18, 20, the ledges 26, and the recessed portion 28 may be recessed from the peripheral surfaces 24, wherein the depths d1, d2, d3, d4 are defined as a distance between the peripheral surface 24 to a surface of the first chamber 18, the second chamber 20, the ledges 26, and the recessed portion 28, respectively. The first and second chambers 18, 20 may be defined by recessed compartments arranged in a non-concentric relationship, which are in fluid communication with each other via the flow path 22.

Figure 3:
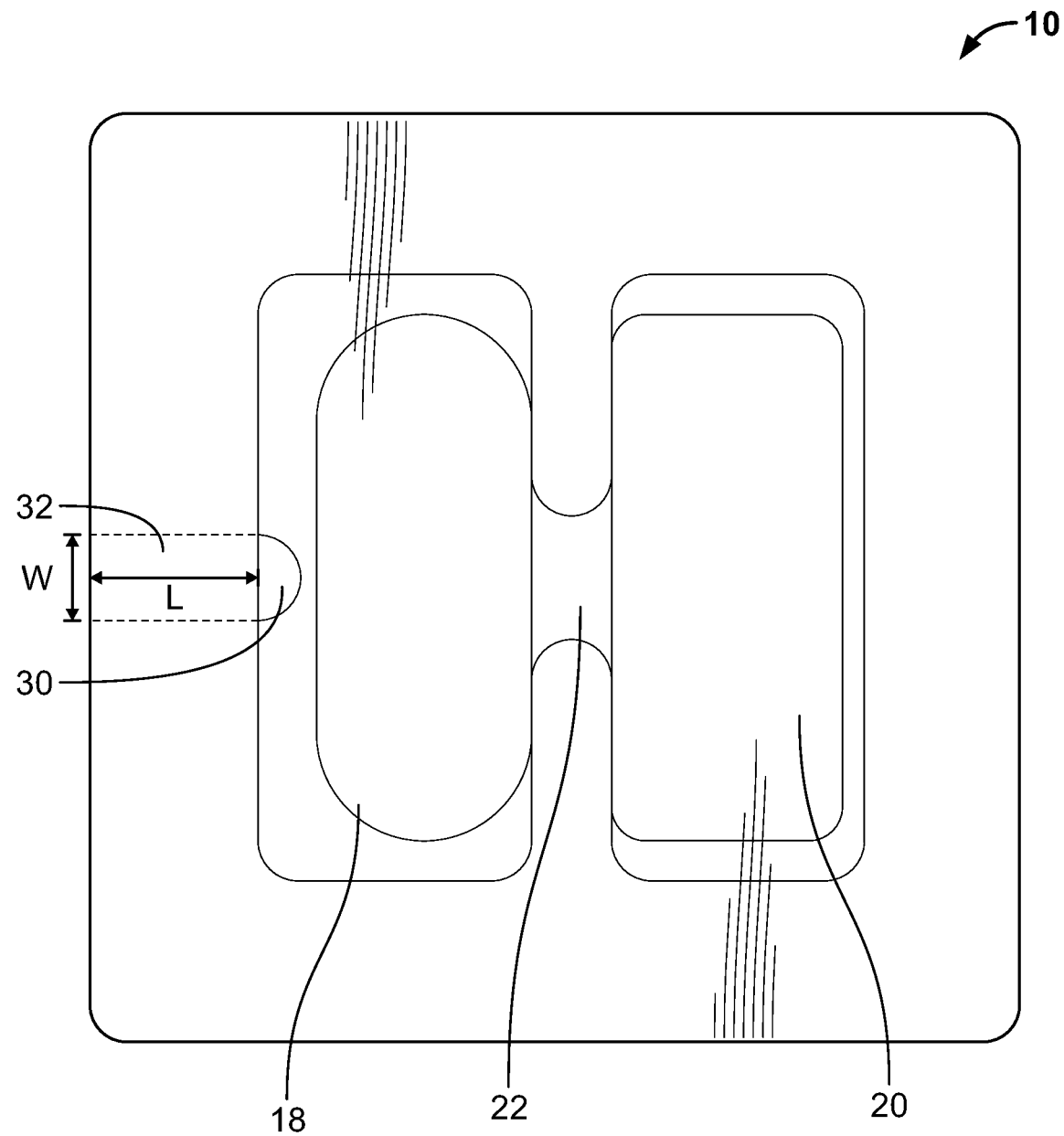
FIG. 3 is a top perspective view of the challenge pack FIG. 1 with a portion of a top cover peeled off.

The first cover 14 may be configured such that it may be placed on the ledges 26, generally flush against the peripheral surfaces 24 to cover the first and second chambers 18, 20. The first cover 14 including the notch 30 may be arranged on the ledges 26, such that when the second cover 16 is placed over the first cover 14 and sealed to the peripheral surface 24, the notch 30 is aligned with the unsealed portion 32 to provide a restrictive fluid path from the outer environment into the first chamber 18 through the unsealed portion 32 and the notch 30, as best shown in FIGS. 3 and 4.

The first cover 14 may include a first portion 34 and a second portion 36, which are connected by a relatively narrow middle portion 38. The first portion 34 may have a generally rectangular shape and configured to cover the first chamber 18. The second portion 36 may also have a generally rectangular shape and configured to cover the second chamber 20. The notch 30 may be provided in the first portion 34 proximate an outer peripheral edge 39, such that when the first cover 14 is place on the ledges 26, the notch 30 may be aligned with the unsealed portion 32 between the peripheral surface 24 and the second cover 16, and may extend beyond the ledge 26 and into the first chamber 18 to define a restrictive fluid path from the exterior environment into the first chamber 18.

In an embodiment, the notch 30 may be defined by a generally semicircular cut out having a diameter of about ¼ inch to about 1 inch, and preferably about ¾ inch. For example, the notch 30 may be defined by a semicircular cut-out having a diameter of about 5/16 inch. In other embodiments, the notch may be defined by one or more cut-outs having various shapes, such as a rectangle, triangle, etc., and configured such that at least a portion of the notch extends into the first chamber 18 to provide fluid communication between the exterior environment and the first chamber through the unsealed portion 32 and the notch 30.

The first cover 14 may be provided as a generally flat and relatively stiff structure, such that when the peripheral edges of the first cover 14 is place on the ledges 26, the first cover 14 may remain generally flat and undeflected during and after a sterilization process. In an embodiment, the first cover may be formed from a suitable polymeric material having a thickness of about 0.05 inch to about 0.1 inch. Suitable materials for the first cover 14 may include, but not limited to, polypropylene, polyester, polycarbonate, polyolefin, polystyrene, polyacrylamide, polymethacrylate, poly(methyl)methacrylate, polyimide, polybutylene terephthalate and polyvinylchloride, metal, aluminum, and cardboard.

The ledges 26 may be defined by relatively narrow surfaces arranged between the peripheral surfaces 24 and the first and second chambers 18, 20, recessed from the peripheral surfaces 24 and surrounding at least some outer peripheries of the first and second chambers 18, 20, such that outer peripheries of the first cover 14 may be placed on the ledges 26. Depth d3 of the ledges 26 may be about equal or greater than a thickness of the first cover 14. In an embodiment, the depth d3 of the ledges 26 may be about equal to the thickness of the first cover 14, such that when the first cover 14 is placed on the ledges 26 to cover the first and second chambers 18, 20, the top surface of the first cover 14 may be even leveled with the peripheral surface 24 as shown in FIG. 4.

In the embodiment of FIGS. 1-4, the first cover 14 may be configured such that when the first cover 14 is placed on the ledges 26, the middle portion 38 is arranged over the recessed portion 28 of the base tray 12. The flow path 22 between the first and second chambers 18, 20 may be defined by a gap between the middle portion 38 of the first cover 14 and the recessed portion 28 of the base tray 12. In such an embodiment, depth d4 of the recessed portion 28 may be greater than depth d3 of the ledges 26, such that when the first cover 14 is place on the ledges 26, a gap may be provide between the middle portion 38 and the recessed portion 28 to allow fluid communication between the first and second chambers 18, 20.

The base tray 12 may be formed from a suitable polymer, such as polycarbonate, polyolefin (e.g., polypropylene), polystyrene, polyacrylamide, polymethacrylate, poly(methyl)methacrylate, polyimide, polyester, polyethylene terephthalate, polybutylene terephthalate and polyvinylchloride, and combinations thereof. In an embodiment, the base tray 12 may be formed from polypropylene or polycarbonate having a thickness of about 0.05 inch to about 0.1 inch.

The challenge pack 10 may also include the second cover 16 attached to the peripheral surface 24 of the base tray 12 forming a sealed enclosure for the first and second chambers 18, 20 with the unsealed portion 32 being the only access into the first and second chambers. The second cover 16 may be attached to the peripheral surface 24 via an adhesive, heat seal, sonic weld, magnetic induction seal, or other known methods, which may be configured to provide a complete seal between the internal spaces within the test pack, e.g., the first and second chambers, and the external environment, except at the unsealed portion 32, which is left unattached to the peripheral surface 24. The second cover 16 may be attached to the base tray 12, such that the second cover 16 remains securely attached to the base tray 12 during and after a sterilization process, such as steam sterilization in an autoclave, but may be peeled away by a user to provide access to the biological indicator and/or chemical indicator. The unsealed portion 32 may be configured to allow a restricted flow of a gaseous sterilization medium into the first and second chambers 18, 20. In an embodiment, the unsealed portion 32 may have a length L of about ¾ inch to about 1.25 inch, preferably about 1 inch, and a width W of about ¼ inch to about 1 inch, preferably about ¾ inch. For example, the unsealed portion 32 may have a length L of about 1 inch and a width W of about ¾ inch.

In some embodiments, the sterilization challenge pack may be used in gravity sterilization cycles, chemical sterilization cycles or gas sterilization cycles, such as ethylene oxide sterilization cycles. In such embodiments, the first cover may be not be necessary as the risk of the second cover collapsing into the chambers during a sterilization cycle is low. Thus, the sterilization challenge pack may be configured with only one cover, i.e. the second cover. Accordingly, the challenge pack may also be configured to be free of any ledges for placement of the first cover. In such an embodiment, the unsealed portion between the second cover and the base tray may have a length L of about ¾ inch to about 1.25 inch, preferably about 1 inch, and a width W of about 1/32 inch to about 1 inch, preferably about ¼ inch.

The second cover 16 may be formed from a suitable material, such as one or a combination of two or more of metal foil (e.g. aluminum foil), metallized foil, polyester, polyolefin (e.g. polyethylene, polypropylene), polycarbonate, polystyrene, polyacrylamide, polymethacrylate, poly(methyl)methacrylate, polyimide, polyamide, polyethylene terephthalate, polybutylene terephthalate, polyvinylchloride and cardboard. In an embodiment, the second cover 16 may be formed from a clear polyester film. In another embodiment, the second cover 16 may be formed from a metal foil. In some embodiments, the second cover 16 may be formed from an autoclaveable polyester foil peelable laminate, such as TOLAS™ ITD-6121 laminate. The laminate material may include multiple layers, for example, a layer of polyester, a layer of foil and a layer of a sealant film laminated with intervening adhesive layers. In an embodiment, the second cover 16 may be formed from a laminate material having a polyester outer layer, an aluminum foil inner layer, and a high density polyethylene sealing layer. The laminate material may have a thickness of about 0.002 inch to about 0.005 inch.

In an embodiment, the challenge pack 10 may be configured such that the chemical indicator is visible from outside, so that a user may check the chemical indicator without removing the top cover 16. In such an embodiment, the first and second covers 14, 16 may be formed from a clear plastic material and/or the base tray 12 may be formed from a clear plastic material to facilitate viewing of the chemical indicator from outside the challenge pack 10.

In use, the challenge pack 10 may be placed in a sterilization chamber along with the objects to be sterilized. During a sterilization process, steam or other gaseous sterilization medium may enter the first and second chambers 18, 20 through the unsealed portion 32 and the notch 30 in the first cover 14. As the sterilization process continues, the steam or other gaseous sterilization medium permeates into the biological and chemical indicators. The challenge pack 10 may be configured such that the unsealed portion 32 and the notch 30 provides a restrictive flow path for the steam or other gaseous sterilization medium that more closely mimic the restrictive flow path into the center of 16-towel test pack when compared to prior art challenge packs, such as the test pack disclosed in U.S. Pat. No. 9,017,994. During some sterilization processes, a vacuum may be drawn in the sterilization equipment (and thus in the sterilization process challenge pack 10), following which the sterilization medium is introduced into the sterilization equipment (and thus the challenge pack 10.)

Some prior art challenge packs include an absorber or other sterilant-reactive device to restrict the flow of gaseous sterilization medium into the chambers containing biological and/or chemical indicators. The challenge pack 10 may be configured to provide a restrictive flow path that closely mimics the path to the center of 16-towel pack without requiring an absorber or other similar devices for further restricting flow of the gaseous sterilization medium.

Challenge pack samples configured according to the embodiments disclosed in the present disclosure and including an unsealed portion having a width of about ¼ inch and a length of about 1 inch or a width of about ⅜ inch and a length of about 1 inch were tested in various autoclave cycles. Test results showed positive biological activity (live biological activity) at 1 min, 2 min, and 4 min sterilization cycles indicating that the challenge pack samples provided sufficient flow resistance to mimic the flow resistance to the center of 16-towel pack.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A sterilization challenge pack for determining the efficacy of a sterilization process, comprising: a base tray including a first chamber, a second chamber and a peripheral surface, the first and second chambers being in fluid communication with each other; a first cover including a notch and configured to cover the first and second chambers; a second cover attached to the peripheral surface except at an unsealed portion; a sterilization indicator contained in one of the first and second chambers; wherein the base tray includes ledges defined by surfaces recessed from the peripheral surface and arranged between the peripheral surface and the first and second chambers, wherein the first cover is arranged on the ledges and configured such that the notch extends beyond the ledges and into the first chamber when placed on the ledges, wherein the only fluid communication between the first and second chambers and an external environment is provided through the unsealed portion and the notch, wherein the sterilization challenge pack is configured to restrict a flow path of steam or a gaseous sterilization medium into the first and second chambers to determine whether a sterilization process has occurred, and wherein the unsealed portion and the notch are configured to restrict the flow path for the steam or the gaseous sterilization medium, into the first chamber.

2. The sterilization challenge pack of claim 1, wherein the sterilization indicator includes a biological indicator and a chemical indicator, wherein the biological indicator is contained in the first chamber and the chemical indicator is contained in the second chamber.

3. The sterilization challenge pack of claim 1, wherein the first cover includes a first portion configured to cover the first chamber and the second portion configured to cover the second chamber, wherein the first and second portions are connected by a middle portion.

4. The sterilization challenge pack of claim 1, wherein the notch is provided in the first portion proximate an outer peripheral edge, wherein the first cover is arranged on the ledges such that the notch is aligned with the unsealed portion to provide a fluid path into the first chamber through the unsealed portion and notch.

5. The sterilization challenge pack of claim 1, wherein the base tray includes a recessed portion between the first and second chambers, wherein the first cover is configured such that when the first cover is placed on the ledges, the middle portion is arranged over the recessed portion, wherein the ledges has a first depth and the recessed portion has a second depth, wherein the second depth is greater than the first depth, such that a gap is provided between the middle portion of the first cover and the recessed portion of the base tray to provide a fluid path between the first and second chambers.

6. The sterilization challenge pack of claim 1, wherein the unsealed portion extends from an outer periphery of the second cover to the notch, wherein the unsealed portion is configured to provide a flow path having a width of about ¼ inch to about 1 inch.

7. The sterilization challenge pack of claim 1, wherein the notch is defined by a generally semicircular cut out, wherein the notch has a diameter of about ¼ inch to about 1 inch.

8. The sterilization challenge pack of claim 1, wherein the base tray is thermoformed from a thermoplastic polymer.

9. The sterilization challenge pack of claim 1, wherein the second cover is sealed to the peripheral surface via an adhesive or heat seal, wherein the second cover is left unsealed to the peripheral surface in the unsealed portion.

10. The sterilization challenge pack of claim 1, wherein the second cover is formed from a laminate material having a metal foil layer and a sealing layer, wherein the second cover is heat sealed to the peripheral surface except in the unsealed portion.

11. The sterilization challenge pack of claim 1, wherein the first and second chambers are in a substantially parallel side by side relationship, wherein a flow path from the external environment to the first chamber is provided through the unsealed portion and notch.

12. The sterilization challenge pack of claim 1, wherein the base tray or the first and second covers, or the base tray and the first and second covers are formed from a sufficiently transparent material such that the at least one sterilization indicator is visible from outside the sterilization challenge pack.

* * * * *